United States Patent
Yao

(10) Patent No.: US 9,931,183 B2
(45) Date of Patent: Apr. 3, 2018

(54) ORTHODONTIC CORRECTION DEVICE

(71) Applicant: DENSMART DENTAL CO., LTD., Taoyuan (TW)

(72) Inventor: Yin Chao Yao, Taoyuan (TW)

(73) Assignee: DENSMART DENTAL CO., LTD., Taoyuan (TW)

( * ) Notice: Subject to any disclaimer, the term of this patent is extended or adjusted under 35 U.S.C. 154(b) by 13 days.

(21) Appl. No.: 14/704,728

(22) Filed: May 5, 2015

(65) Prior Publication Data

US 2015/0366642 A1  Dec. 24, 2015

(30) Foreign Application Priority Data

Jun. 19, 2014 (TW) .............................. 103210781 U

(51) Int. Cl.
| | |
|---|---|
| *A61C 3/00* | (2006.01) |
| *A61C 8/00* | (2006.01) |
| *A61C 7/12* | (2006.01) |
| *A61C 7/30* | (2006.01) |

(52) U.S. Cl.
CPC .............. *A61C 8/0096* (2013.01); *A61C 7/12* (2013.01); *A61C 7/303* (2013.01)

(58) Field of Classification Search
CPC ...... A61C 8/0006; A61C 8/0007; A61C 7/008
USPC .......................................................... 433/18
See application file for complete search history.

(56) References Cited

U.S. PATENT DOCUMENTS

| | | | | |
|---|---|---|---|---|
| 4,861,268 A | * | 8/1989 | Garay ................. | A61C 19/063 424/435 |
| 5,018,259 A | * | 5/1991 | Wildman ............... | A61C 7/12 216/33 |
| 5,055,039 A | * | 10/1991 | Abbatte ................ | A61C 7/146 433/24 |
| 5,078,597 A | * | 1/1992 | Caplin .................... | A61C 7/16 433/18 |
| 5,176,517 A | * | 1/1993 | Truax ....................... | A61C 7/12 433/180 |
| 5,184,954 A | * | 2/1993 | Hanson ................ | A61C 7/303 433/11 |
| 5,820,368 A | * | 10/1998 | Wolk ...................... | A61C 7/02 433/141 |
| 5,853,291 A | * | 12/1998 | DeVincenzo ....... | A61B 17/663 433/176 |
| 5,938,437 A | * | 8/1999 | DeVincenzo .......... | A61C 7/00 433/18 |

(Continued)

*Primary Examiner* — Cris L Rodriguez
*Assistant Examiner* — Matthew Saunders
(74) *Attorney, Agent, or Firm* — Rabin & Berdo, P.C.

(57) ABSTRACT

An orthodontic correction device set up within an oral cavity of a patient. It includes a bone screw member that has a plate, the plate includes at least a positioning portion, and a surface of the plate includes at least a fixing member; at least a bone screw is in connection with at least a positioning portion of the bone screw member, and that is fixed by implanting into the oral cavity; at least a base body is assembled on a surface of the teeth and including a connecting portion; and at least an elastic member, a fixing end of the elastic member is assembled and fixed on the fixing member of the bone screw member, a functioning end of the elastic member is in mutual connection with the connecting portion of the base body, and an orthodontic correction force is formed between the fixing end and the functioning end.

6 Claims, 17 Drawing Sheets

(56) References Cited

U.S. PATENT DOCUMENTS

| | | | | |
|---|---|---|---|---|
| 5,967,772 A * | 10/1999 | Gray | A61C 7/00 | 433/18 |
| 6,183,250 B1 * | 2/2001 | Kanno | A61C 7/28 | 433/17 |
| 6,193,509 B1 * | 2/2001 | DeVincenzo | A61C 7/00 | 433/173 |
| 6,354,833 B1 * | 3/2002 | Townsend-Hansen | A61C 7/14 | 433/24 |
| 6,827,574 B2 * | 12/2004 | Payton | A61C 7/00 | 433/173 |
| 7,281,923 B1 * | 10/2007 | DeVincenzo | A61B 17/8061 | 433/173 |
| 7,780,444 B1 * | 8/2010 | Schendel | A61C 7/00 | 433/174 |
| 8,403,663 B2 * | 3/2013 | Hilgers | A61C 7/00 | 433/18 |
| 8,807,998 B2 * | 8/2014 | Lee | A61C 7/00 | 433/18 |
| 2003/0044746 A1 * | 3/2003 | Marotta | A61C 7/14 | 433/18 |
| 2004/0023182 A1 * | 2/2004 | Lin | A61C 7/00 | 433/18 |
| 2004/0067464 A1 * | 4/2004 | Lin | A61B 17/8685 | 433/18 |
| 2004/0166460 A1 * | 8/2004 | Devincenzo | A61C 8/00 | 433/18 |
| 2005/0142513 A1 * | 6/2005 | Hotta | A61C 7/00 | 433/18 |
| 2005/0147938 A1 * | 7/2005 | Devincenzo | A61C 8/0031 | 433/18 |
| 2006/0069389 A1 * | 3/2006 | Knopfle | A61C 8/0031 | 433/24 |
| 2006/0257811 A1 * | 11/2006 | Ohki | A61C 7/10 | 433/18 |
| 2007/0259306 A1 * | 11/2007 | Raines, Jr. | A61C 7/00 | 433/18 |
| 2008/0248441 A1 * | 10/2008 | De Clerck | A61C 7/00 | 433/18 |
| 2008/0254401 A1 * | 10/2008 | Yazdi | A61C 7/00 | 433/18 |
| 2010/0047732 A1 * | 2/2010 | Park | A61C 7/10 | 433/18 |
| 2011/0165532 A1 * | 7/2011 | Benvegnu | A61C 7/00 | 433/18 |
| 2013/0052605 A1 * | 2/2013 | Ahn | A61C 7/00 | 433/18 |
| 2014/0363778 A1 * | 12/2014 | Parker | A61C 7/146 | 433/3 |

* cited by examiner

ORTHODONTIC CORRECTION DEVICE

FIELD OF THE INVENTION

The present invention relates generally to a dental appliance that provides an orthodontic force for the correction of the teeth of a patient, and more particularly, the present invention relates to an orthodontic correction device that is able to simultaneously exert a corrective force on a number of teeth, or relates to an orthodontic correction device that can exert different corrective forces on a single tooth of the patient.

BACKGROUND OF THE INVENTION

FIG. 1 and FIG. 2 show the orthodontic bone screw device for implantation 1. The orthodontic appliance 10 is commonly used when patients need to undergo orthodontic treatment, and in this situation, the orthodontic appliance 10 will be sleeved by an orthodontic metal wire 11 in order to provide a horizontal, vertical and sagittal directional force to the teeth of the patient. However, if the situation of the patient's teeth is such that the teeth are severely misaligned, or if the patient's teeth are only partially misaligned, then the dental surgeon will further implant a bone screw 12 in accordance with the correction requirements of the individual patients. In addition, the orthodontic treatment offered by the dental surgeon involves assembling an elastic fixing member 13 in between the bone screw 12 and the orthodontic appliance 10, As shown in FIG. 1 and FIG. 2, the orthodontic bone screw device for implantation 1 is set up on the jaw bone of the oral cavity of the patient, and includes a bone screw 12 and an elastic fixing member 13. The bone screw 12 includes a disc-shaped cap portion 12a, and includes a screw portion 12b that extends downwards on the same axis from disc-shaped cap portion 12a and having screws on its external surface. Furthermore, the bone screw 12 also includes a neck portion 12c that projects coaxially from the top surface of the cap portion 12a, and the outer diameter of the neck portion 12c is smaller than the outer diameter of the cap portion 12a. In addition, the bone screw 12 also includes a head portion 12d that is fixed on to top surface of the neck portion 12c, and the outer diameter of the head portion 12d is larger than the outer diameter of the neck portion 12c.

The outer diameter of the screw portion 12b tapers gradually from the top to the bottom. The outer diameter of the head portion 12d tapers gradually from bottom to the top, and the top surface of the head portion 12d is in the shaped of a convex arc.

The elastic fixing member 13 is an object that has elasticity and that may be elastically extended, and may include a number of positioning portions 131 that are linked integrally into one body. Each of the positioning portions 131 has a positioning hole 131a, and any one of the positioning portion 131 is used for sleeving the neck portion 12c that has been set up on the bone screw 12.

FIG. 2 is a schematic diagram showing the use of the orthodontic bone screw device for implantation 1. When the bone screw 12 is being used, the bone screw 12 is used in conjunction with a rotating tool. The rotating tool may be set up on the head portion 12d and the neck portion 12c. The rotating tool is driven in order to perform the rotational action of the bone screw 12, and as a result enables the screw portion 12b of the bone screw 12 to turn, to be drilled and be locked in the jaw bone, or be detached from the jaw bone. Moreover, the orthodontic appliance 10 and the orthodontic metal wire 11 need to be set up/assembled on to the teeth of the patient, and this is followed by passing one of the positioning holes 131a of the elastic fixing member 13 that is adjacent to the orthodontic metal wire 11 through the hook portion 11a of the orthodontic metal wire 11, so as to select any one of positioning holes 131a of the elastic fixing member 13 to be sleeved on to the bone screw 12. Subsequent to the completion of the above-mentioned set up, a pulling force exerted in any particular direction is provided to the elastic fixing member 13 by means of the bone screw 12, in order to achieve the effects of the orthodontic correction.

However, although the orthodontic metal wire 11 of the above-mentioned device may provide a pulling force that is exerted in a left and right direction in different orthodontic appliances, but if in a situation where a patient's teeth are severely misaligned, then patient still needs multiple implantations of the bone screw in order to achieve the required level of orthodontic correction for a number of teeth at the same time. Furthermore, the implantation of the bone screw is not able to allow the individual tooth of the patient to be subjected to the torque force. As such, from the point of view of the dental surgeon, this orthodontic treatment method is not only extremely inconvenient, it also causes the orthodontic treatment procedure to be more complex, also increasing the dangers of the surgery. In addition, from the view point of the patient, the method of orthodontic treatment of their teeth that involves multiple implantations of the bone screw is an orthodontic treatment method that increases pain and fear.

SUMMARY OF THE INVENTION

The main objective of the present invention is to provide an orthodontic correction device, and the use of the orthodontic device of the present invention involves setting up the bone screw plate in the oral cavity of the patient, and is used in conjunction with an elastic member that has a pushing force or a pulling force, and is also used in conjunction with a fixing member, whereby the directions of the forces may be determined by means of the use of the fixing member in accordance with the corrective force requirements. In addition, the orthodontic correction device of the present invention may exert a corrective force on a number of teeth, or may exert a corrective force on a single tooth in different directions at the same time. Moreover, the orthodontic correction device is able to straighten misaligned teeth that are in any location at the same time. As such, the number of bone screws that are implanted into the jaw bone of patients may be reduced.

The other objective of the present invention is that the orthodontic correction device of the present invention enables the number of bone screws that need to be implanted into the bone of the oral cavity of patients to be reduced, and as such enabling the risks of the surgery to be reduced. Furthermore, the bone screw that originally needs to be set up in the lingual side of the oral cavity of the patient is mostly replaced by orthodontic correction device of the present invention, which exists on the palatal side of the oral cavity of the patient. This also has the effect of preventing and reducing the damage caused to the dental root of the patient when the bone screw is implanted in the lingual side of the bone of the oral cavity of the patient.

Additionally, yet another objective of the present invention enables the fixing member of the orthodontic correction device to be adjusted by means of setting up direction of the fixing member, on the basis of the corrective force exerted and the corrective force that is required, and as such achieving the most preferable force and position, as well as balancing force that are required for the correction of teeth that are not straight.

In order to achieve the objectives of the present invention, the orthodontic correction device of the present invention is set up within the oral cavity of the patient, so as to correct the arrangement of a patient's teeth. The orthodontic correction device of the present invention includes a bone screw plate, which has a plate, whereby the plate includes at least a positioning portion, and the surface of the plate includes at least a fixing member; at least a bone screw, which is in connection with the positioning portion of the bone screw plate, and is fixed by implanting into the oral cavity of the patient; at least a base body, which is assembled on the surface of the teeth, and includes a connecting portion; and at least an elastic member, which includes a fixing end and a functioning end, whereby the fixing end is assembled on the fixing member of the bone screw plate, and whereby the functioning end is assembled in the connecting portion of the base body. Moreover, an orthodontic correction force is formed between the fixing end and the functioning end.

The fixing member includes a base portion and an engagement portion, whereby one side of the base portion may be adjacent to the surface of the plate, and the other side of the base portion may be in connection with an engagement portion, and the engagement portion may be in connection with the fixing end of the elastic member.

In accordance with the first preferred exemplary embodiment of the present invention, the engagement portion may include at least a hook, and the elastic member may include at least a housing aperture that is fixed on the hook.

In accordance with the second preferred exemplary embodiment of the present invention, the engagement portion may include at least a through hole, and in addition, the engagement portion further comprises an opening that is in connection with the through hole. Also, the elastic member may be configured as an orthodontic wire body, and the orthodontic wire body is bent and fixed at the through hole. The orthodontic wire body forms an elastic portion by bending in between the fixing end and the functioning end.

In accordance with the third preferred exemplary embodiment of the present invention, the orthodontic wire body may include a bending portion that has a bending angle. Furthermore, the connecting portion may be configured as a orthodontic monomer that is in connection with the teeth of a patient.

In addition, in accordance with the fourth preferred exemplary embodiment of the present invention, the orthodontic wire body forms an elastic portion by bending in between the fixing end and the functioning end.

The advantage of the present invention is that the bone screw plate of the orthodontic correction device, by means of the fixing member, may be placed in the direction of the oral cavity of the patient where the corrective force needs to be exerted in order for orthodontic correction of the teeth of the patient to be performed, and this is used in conjunction with a fixing member that has a pushing force or pulling force, so as to enable one tooth or a number of teeth located at different positions within the oral cavity and tooth or teeth of the patient having different orthodontic statuses to be corrected at the same time, by means of an elastic member that is in connection with the bone screw plate. As such, the bone screw plate of the orthodontic correction device is able to significantly increase the efficiency and safety of the orthodontic treatments that are offered by the dental surgeons, enabling the dental surgeon to be able to quickly adjust the exertion of the orthodontic corrective force required for orthodontic correction of patients' teeth and also achieving the expected orthodontic results, while at the same time reducing the pain experienced by patients as a result of multiple implantations of the bone screw into their oral cavities.

In addition to the above, the orthodontic correction device of the present invention can enable the bone screws that were originally set up in the lingual side of the bone of the patient's oral cavity to be replaced, such that the orthodontic correction device of the present invention can now be set up in the palatal side of the oral cavity of the patient, and as such significantly reducing the dangers associated with the surgeries that implant the bone screw into the bone of the patients.

BRIEF DESCRIPTION OF THE DRAWINGS

The present invention can be understood in more detail by reading the subsequent detailed description in conjunction with the examples and preferred exemplary embodiments made to the accompanying drawings, wherein.

DETAILED DESCRIPTION OF THE PREFERRED EMBODIMENT

The accompanying drawings are included to provide a further understanding of the invention, and are incorporated in and constitute a part of this specification. The drawings illustrate the preferred exemplary embodiments of the invention and, together with the description, serve to explain the principles of the invention.

Figure 1:
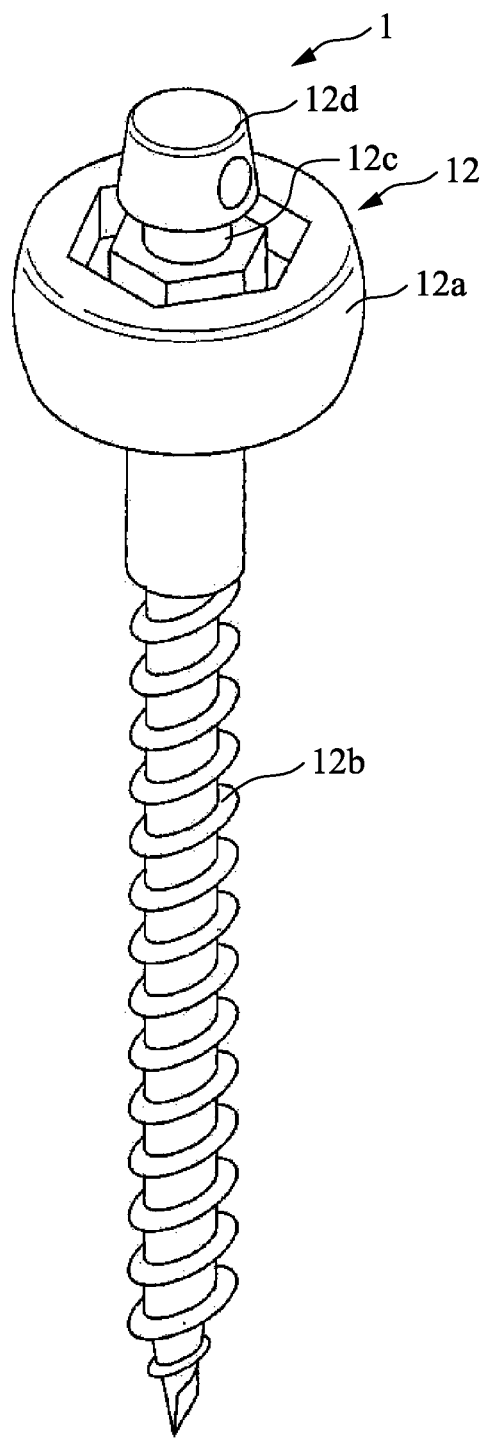
FIG. 1 shows a structural diagram illustrating a conventional orthodontic bone screw device.
Figure 2:
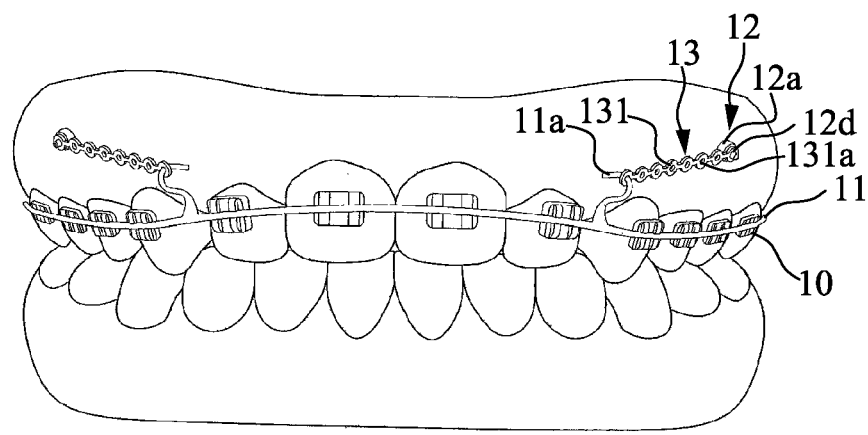
FIG. 2 is a schematic diagram showing the orthodontic bone screw device of FIG. 1 that has been fitted on to the teeth of a patient.
Figure 3:
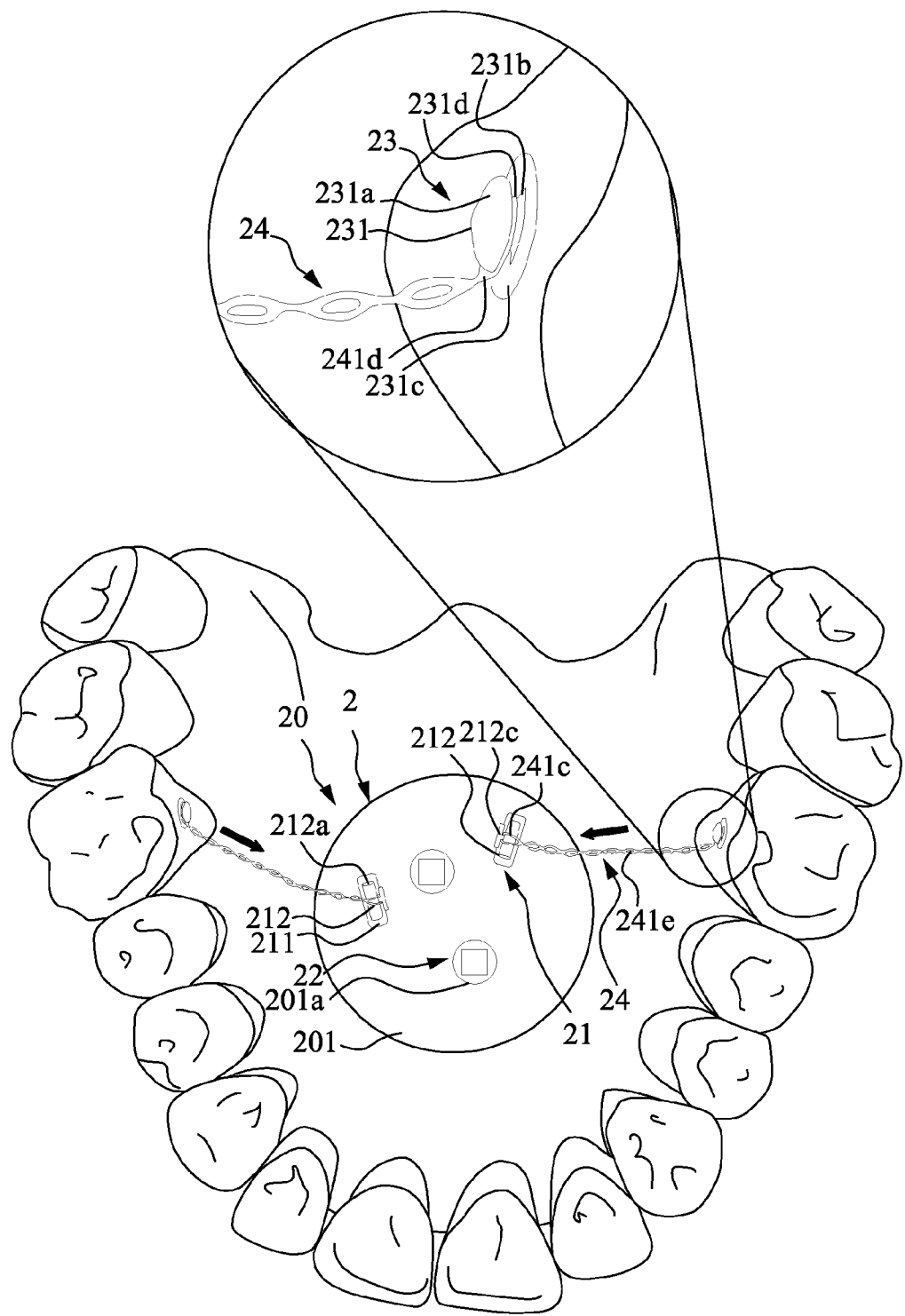
FIG. 3 is a schematic diagram showing the orthodontic correction device in accordance with the first exemplary embodiment of the present invention.

As shown in FIG. 3, in accordance with a first preferred exemplary embodiment of the present invention, the orthodontic correction device 2 of the present invention may be set up within an oral cavity of a patient in order for the arrangement of the patient's teeth to be corrected. The orthodontic correction device 2 of the present invention includes a bone screw plate 20, a fixing member 21, at least a bone screw 22, a base body 23 and at least an elastic member 24. The bone screw plate 20 may have a plate 201. The plate 201 may include at least a positioning portion 201a that can accommodate the at least a bone screw 22.

As shown in FIG. 3, the base body 23 may have a lingual button. The base body 23 may be assembled on a surface of the teeth, and may include a connecting portion 231. The connecting portion 231 may include a head portion 231a, a neck portion 231b that extends downwards from the head portion 231a, a base plate 231c that is bonded to the teeth of a patient. The radial length of the head portion 231a may be greater than the radial length of the neck portion 231b, such that a limiting space 231d that has a groove shape may be formed in between the head portion 231a and the neck portion 231b. In addition, the base body 23 and the at least an elastic member 24 may be mutually connected.

Also referring to FIG. 3, the at least an elastic member 24 may have a fixing end 241c and a functioning end 241d. The fixing end 241c may be assembled in the engagement portion 212 of the fixing member 21 of the bone screw plate 20. The functioning end 241d may be assembled in the neck portion 231b of the connecting portion 231 of the base body 23. In accordance with the first preferred exemplary embodiment of the present invention, the at least an elastic member 24 may be configured in the form of at least a housing aperture 241e, and may also be a structure of continuous housing apertures 241e. In addition, the at least an elastic member 24 may also be a structure that has two housing apertures 241e on both ends of a wire segment. One of the housing apertures 241e that is adjacent to the base body 23 may be fixed in the neck portion 231b of the connecting portion 231 so as to enable one end of the housing apertures 241e to reach the head portion 231a of the connecting portion 231 and to form a limiting space 231d by means of the different radial lengths between the head portion 231a and the neck portion 231b. Moreover, another end of the housing apertures 241e may be fixed on the hook 212c of the fixing member 21.

Figure 4A:
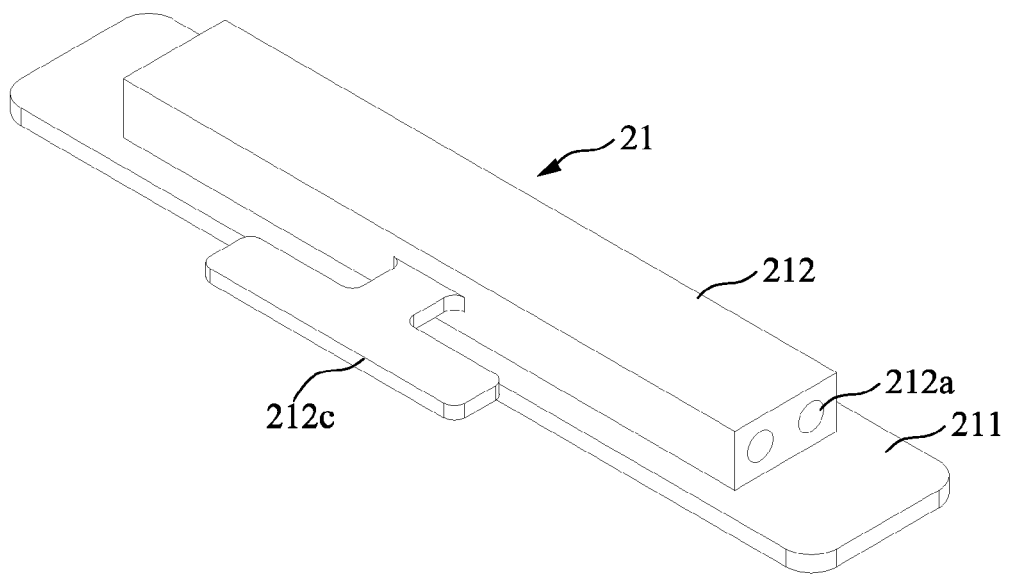
FIG. 4A to FIG. 4B are structural diagrams showing the different forms of fixing members of the orthodontic correction device in accordance with the present invention.
Figure 4B:
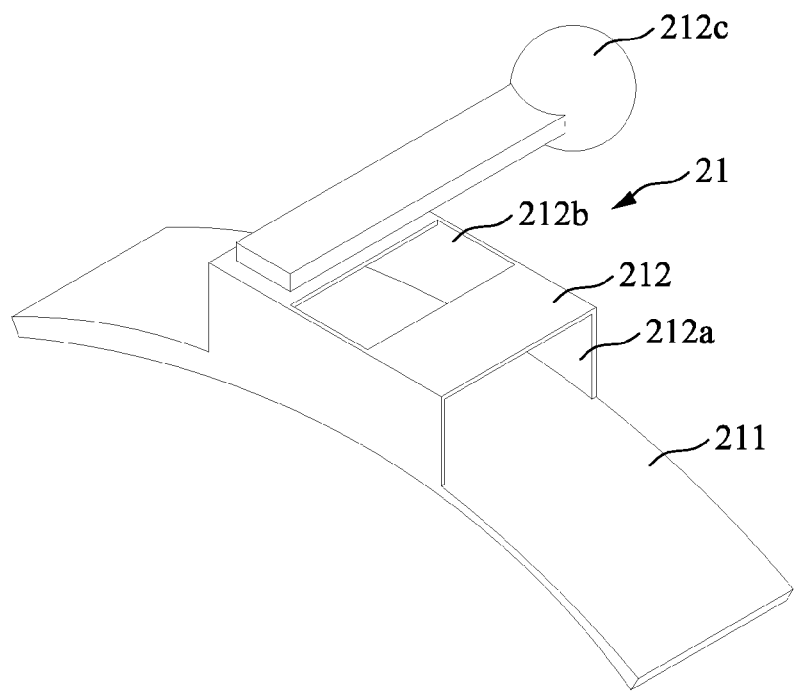

As shown in FIG. 4A and 4B, the fixing member 21 may be configured as different forms in order for it to fit on to different elastic member 24 structures. The fixing member 21 may include a base portion 211 and an engagement portion 212. One side of the base portion 211 may be adjacent to the surface of the plate 201. The other side of the base portion 211 may be in connection with the engagement portion 212. The engagement portion 212 may be in connection with the fixing end 241c of the elastic member 24. In accordance with another preferred exemplary embodiment of the present invention, the engagement portion 212 may include at least a through hole 212a, as shown in FIG. 4A. The at least a through hole 212a may get through to the inside of the engagement portion 212, such that one end of the fixing end 241c of the elastic member 24 may be bent and fixed at the outside portion of the at least a through hole 212a. In addition, the engagement portion 212 may further include an opening 212b that is in connection with the at least a through hole 212a, as shown in FIG. 4B. The elastic members 24 may be mutually fixed at the opening 212b. In accordance with another preferred exemplary embodiment of the present invention, the engagement portion 212 may also include at least a through hole 212a, an opening 212b and at least a hook 212c.

Figure 5A:
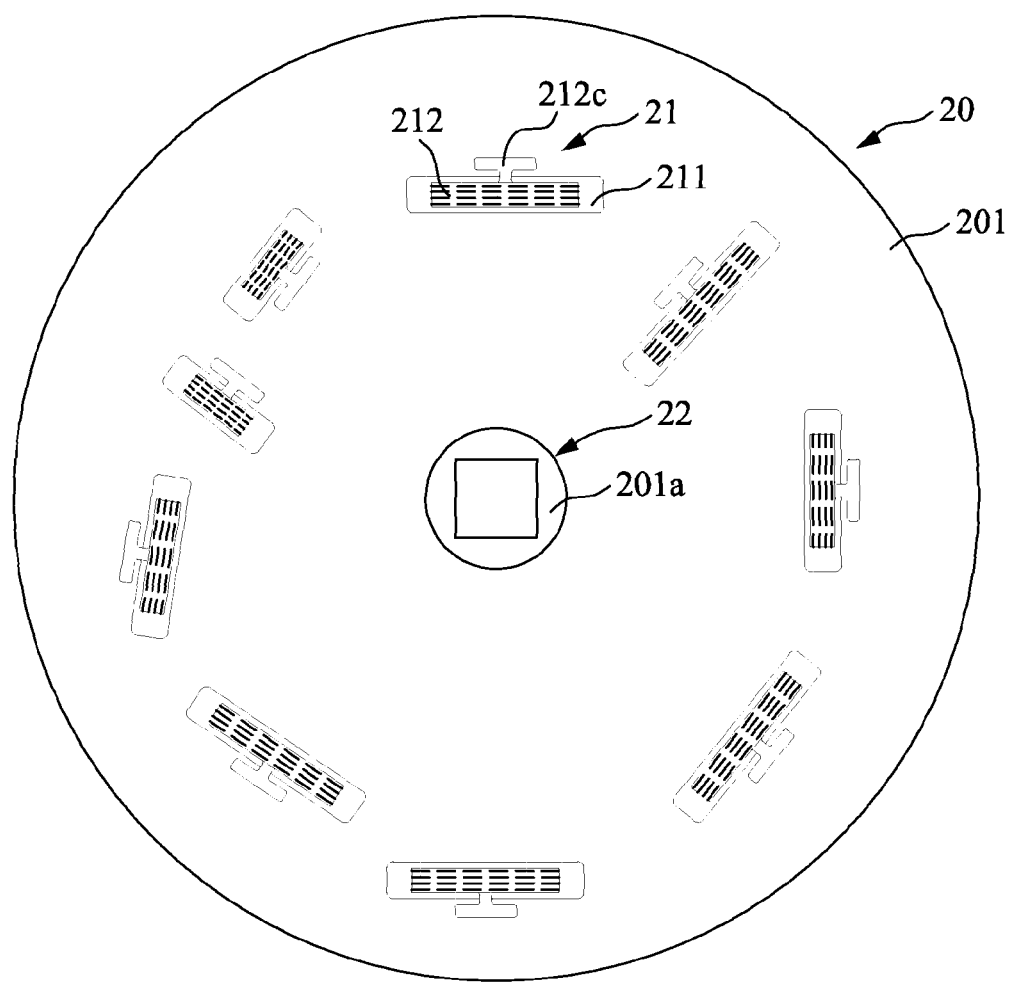
FIG. 5A to FIG. 5B are structural diagrams showing different quantities of fixing members that have been set up in different positions of the bone screw plate of the orthodontic correction device in accordance with the present invention.
Figure 5B:
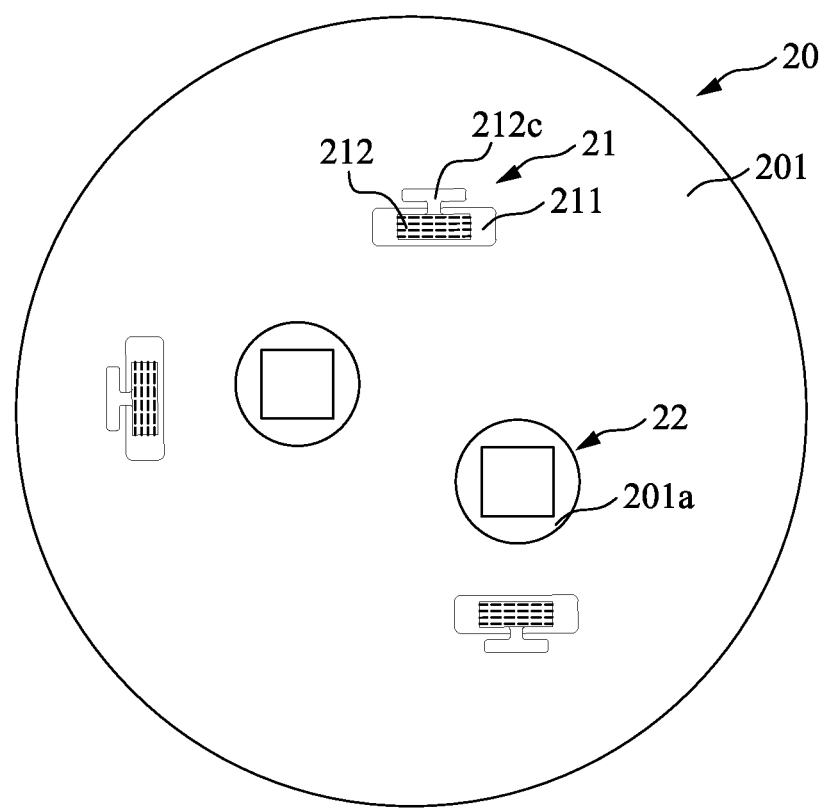

FIG. 5 is a schematic diagram showing that the bone screw plate 20 includes a number of fixing members 21 that have different orientations. The bone screw plate 20 may be fixed within the oral cavity of a patient by means of fixing the bone screw 22. The interior of the oral cavity may include a lingual side, a palatal side as well as a buccal side. In accordance with the orthodontic correction needs of the patient, a dental surgeon may determine the number of bone screw plates 20 that needs to be configured within the oral cavity of the patient. The surface of the plate 201 of the bone screw plate 20 may include at least a fixing member 21. In other words, the at least a fixing member 21 may be configured within the oral cavity of the patient in accordance with the orthodontic correction needs determined by the dental surgeon. That is to say, a dental surgeon may select and decide the number of fixing members 21 that needs be configured on the upper surface of the bone screw plate 20 in accordance with the orthodontic correction needs of the individual patient. As such, the fixing member 21 may be in mutual connection with the elastic member 24 structure. Balance forces may applied to the teeth and the bone screw plate 20 by means of adjusting the orientations of the fixing members 21, as well as adjusting the number of the fixing members 21 in accordance with the variations in the elastic member 24 structures.

In accordance with the use of the first preferred exemplary embodiment of the present invention, and as shown in FIG. 3 to FIG. 5, first of all, the dental surgeon may determine the orthodontic correction status of a patient's teeth, and the positions that require a force to be applied. The dental surgeon may configure different types, orientations and numbers of fixing members 21 on the bone screw plate 20 in accordance with the orthodontic correction status of the patient's teeth. The types of the fixing members 21 may be selected in accordance with the types of the elastic members 24. When a force is applied to enable the teeth of the patient to be pulled towards the inside of the oral cavity, the elastic member 24 may include at least a housing aperture 241e. The elastic member 24 may create tension between the fixing end 241c and the functioning end 241d, by means of tightening up the fixing end 241c and the functioning end 241d of the elastic member 24, so as to enable the teeth of the patient to obtain an applied force towards the inside of the oral cavity. As such, a corrective applied force may be formed between the fixing end 241c and the functioning end 241d.

Figure 6:
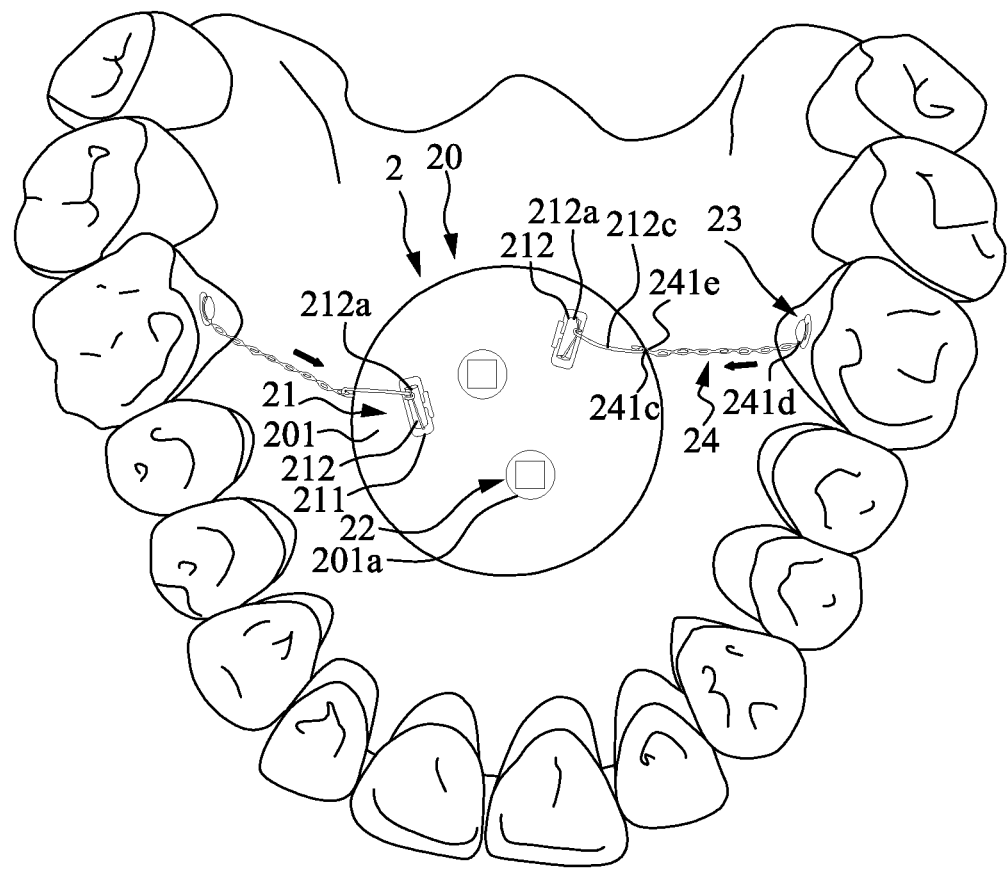
FIG. 6 is another schematic diagram showing the orthodontic correction device of the present invention that is in use, in accordance with the first preferred exemplary embodiment of the present invention.

In accordance with the first preferred exemplary embodiment of the present invention, based on another example, and as shown in FIG. 6, the hook 212c of the engagement portion 212 of the fixing member 21 may also be configured as a hook structure that has two bending regions. Moreover, the hook 212c and the engagement portion 212 may be removable and may be separated from each other. One end of the two bending regions may be fixed on the at least a through hole 212a of the engagement portion 212. Another end of the two bending regions may be in connection with the housing aperture 241e of the elastic member 24. As such, the elastic member 24 may have a tension that is applied to the teeth of the patient in order for orthodontic correction of the patient's teeth to be performed.

Figure 7:
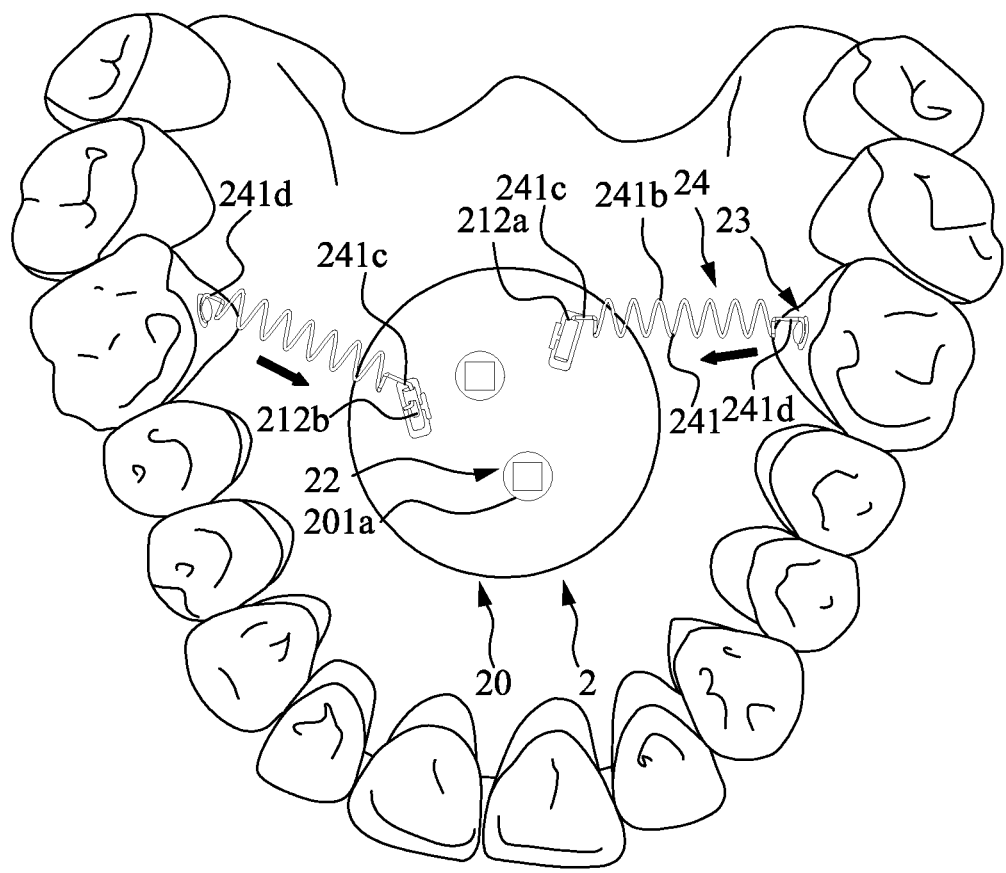
FIG. 7 is a schematic diagram showing the orthodontic correction device that is in use in accordance with the second preferred exemplary embodiment of the present invention.

In accordance with the second preferred exemplary embodiment of the present invention, and as shown in FIG. 7, the elastic member 24 may include an orthodontic wire body 241. The orthodontic wire body 241 may be an inelastic wire or an elastic wire 1. The fixing end 241c of the orthodontic wire body 241 may be fixed at the at least a through hole 212a of the engagement portion 212. In accordance with another example, the engagement portion 212 may further include an opening 212b that is in connection with the at least a through hole 212a. As such, one end of the orthodontic wire body 241 may be directly fixed at the opening 212b. The wire segment area of the orthodontic wire body 241 between the fixing end 241c and the functioning end 241d may be bent to form an elastic portion 241b that is in elastic form. The length of the wire segment between the fixing end 241c and the functioning end 241d of the elastic member 241 may be stretched, so as to enable the elastic portion 241b to form an inward restoring force that has elasticity. As such, the restoring force may carry out an inward correction pushing force on the teeth of the patient.

Figure 8:
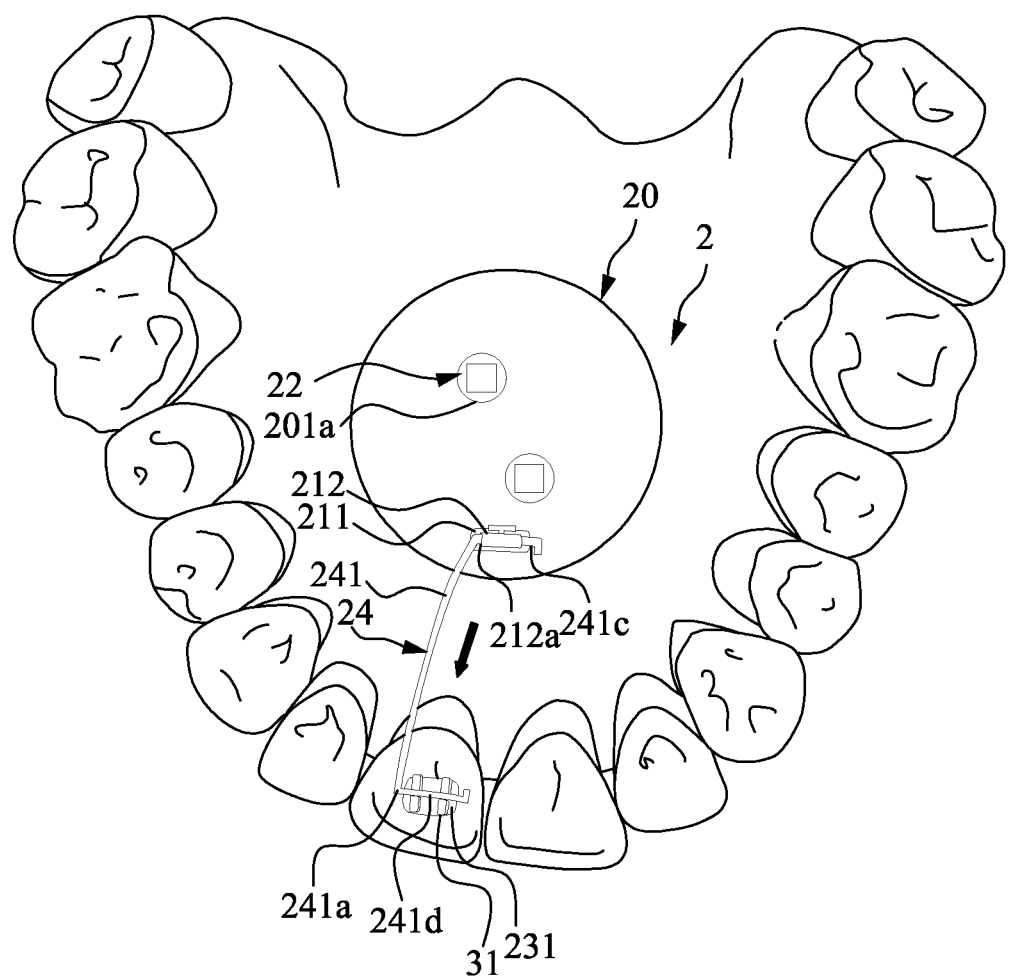
FIG. 8 is a schematic diagram showing the orthodontic correction device that is in use in accordance with the third preferred exemplary embodiment of the present invention.

In accordance with the third preferred exemplary embodiment of the present invention, as shown in FIG. 8, when a dental surgeon would like to carry out an outward correction force on the teeth of a patient, the elastic member 24 may be configured such that it has the same orthodontic wire body 241 as the preferred exemplary embodiment of the present invention. The connecting portion 231 may be configured as an orthodontic correction unit 31. In addition, the orthodontic wire body 241 may include at least a bending portion 241a that has a bending angle so as to enable the orthodontic wire body 241 to form an outward correction pushing force.

Figure 9:
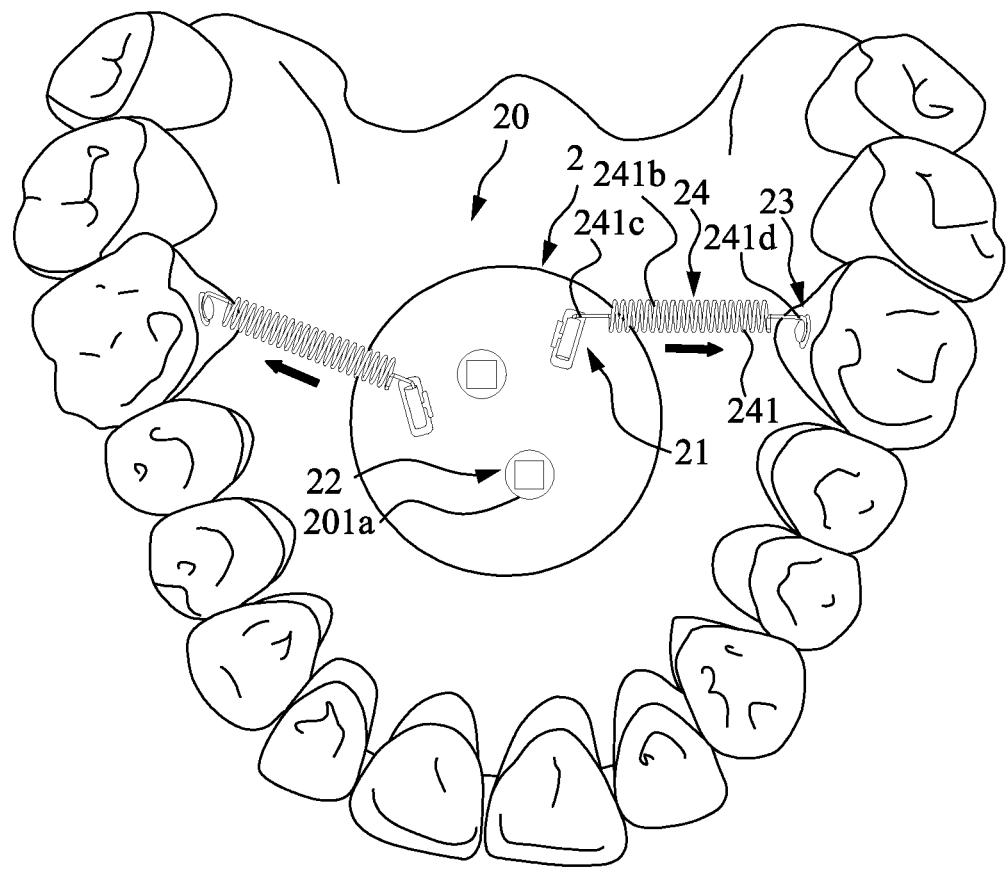
FIG. 9 is a schematic diagram showing the orthodontic correction device that is in use in accordance with the fourth preferred exemplary embodiment of the present invention

In accordance with the fourth preferred exemplary embodiment of the present invention, the elastic member 24 may be configured such that it has the same orthodontic wire body 241 as the second preferred exemplary embodiment of the present invention. The wire segment area between the fixing end 241c and the functioning end 241d of the orthodontic wire body 241 may be bent to form an elastic portion 241b that is in an elastic form. However, the difference between the fourth preferred exemplary embodiment and the second preferred exemplary embodiment is that the length of the wire segment between the fixing end 241c and the functioning end 241d of the elastic member 24 may be compressed by means of the fixing member 21 and the base body 23, as shown in FIG. 9. As such, the elastic portion 241b is enabled to form an elastic outward restoring force. The restoring force may carry out an outward correction pushing force on the teeth of the patient.

Figure 10:
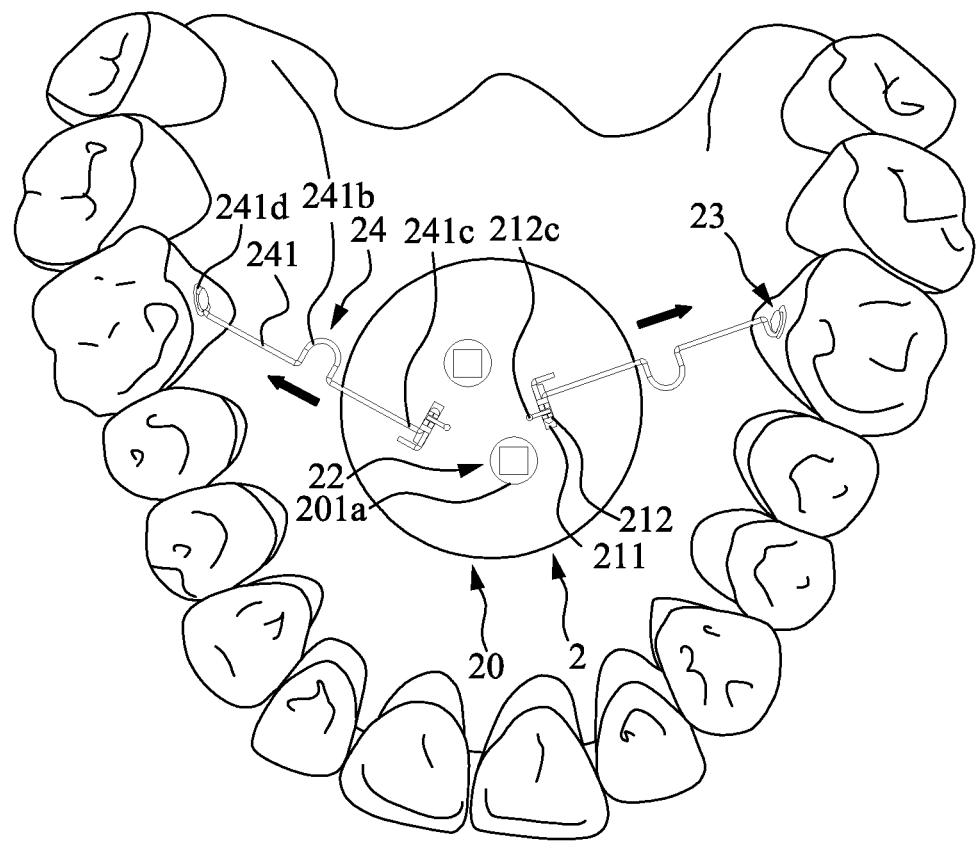
FIG. 10 is another schematic diagram showing the orthodontic correction device that is in use in accordance with the fourth preferred exemplary embodiment of the present invention.

FIG. 10 is a schematic diagram showing another example of the fourth preferred exemplary embodiment of the present invention. The elastic portion 241b of the elastic member 24 may be configured as an arc-shaped structure so as to enable the arc-shaped structure of the elastic portion 241b to have an elastic outward restoring force on the teeth of the patient.

Figure 11:
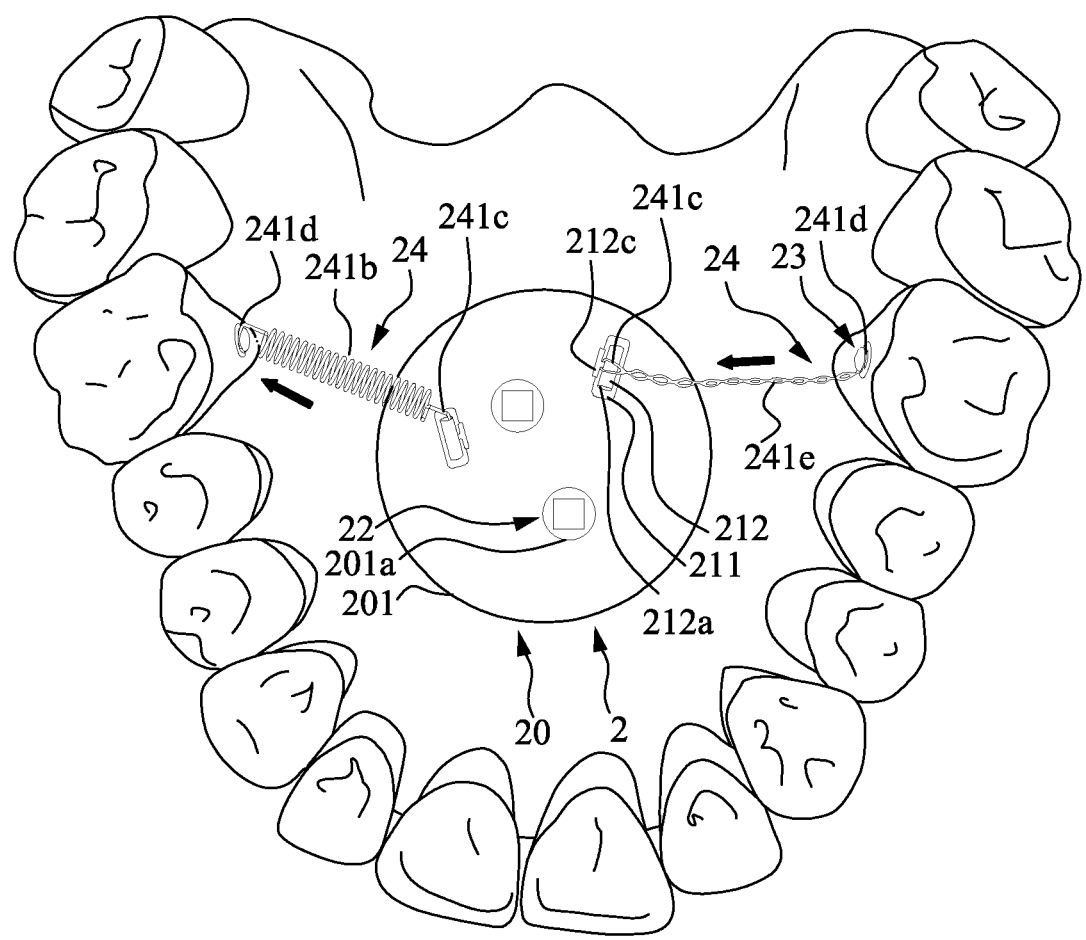
FIG. 11 is a schematic diagram showing the orthodontic correction device that is in use and that carries out a pulling force or a pushing force at the same time, in accordance with the present invention.

The first preferred exemplary embodiment and the preferred exemplary embodiment of the present invention may be carried out at the same time in accordance with the needs of the dental surgeon, as shown in FIG. 11. When the pushing force and the pulling force may be applied to a number of teeth within the oral cavity of the patient by the dental surgeon, the bone screw plate 20 may be configured within the oral cavity, and at least an elastic member 24 that carries out the pushing force and at least an elastic member 24 that carries out the pulling force may be used. As such, the pushing force and the pulling force may be generated for straightening a number of teeth at the same time.

Figure 12:
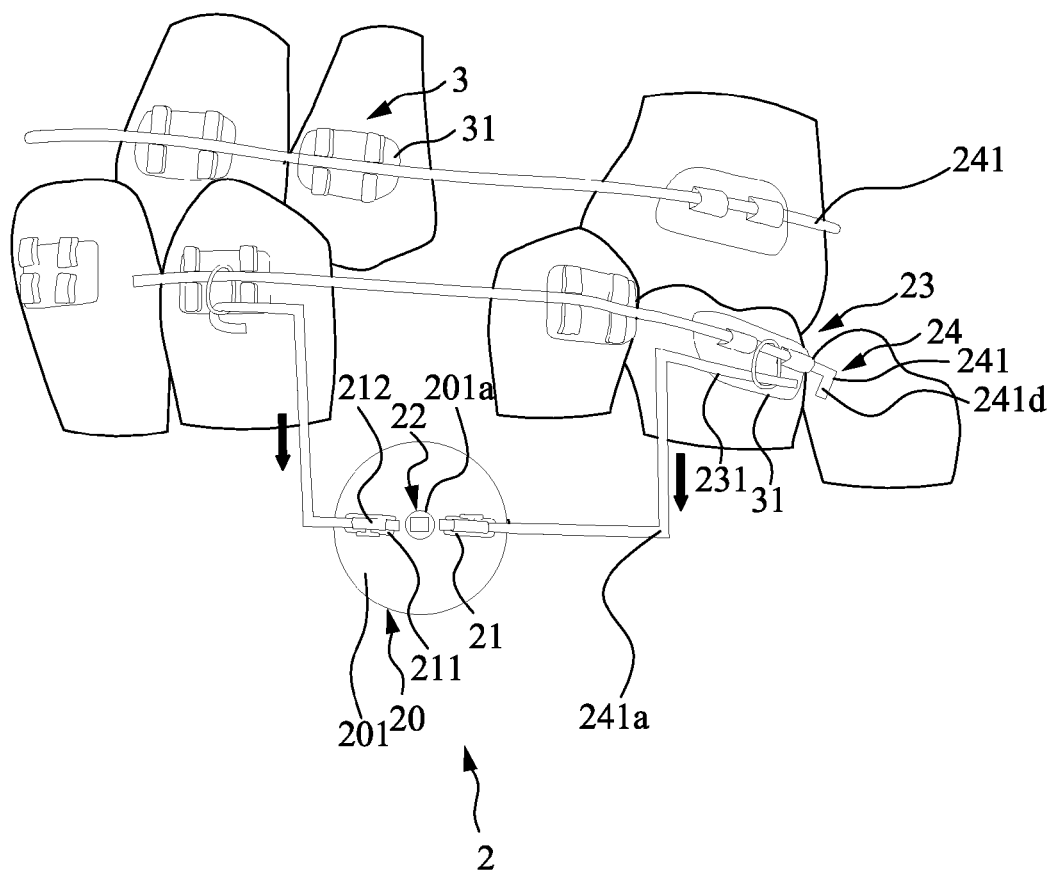
FIG. 12 is a schematic diagram showing the orthodontic correction device that is in use in accordance with the fifth preferred exemplary embodiment of the present invention.

In accordance with the fifth preferred exemplary embodiment of the present invention, and as shown in FIG. 12, in general, when a dental surgeon performs the orthodontic correction of the teeth of a patient, a plurality of orthodontic correction units 31 may be adhered to the surface of the teeth of a patient initially. An orthodontic wire body 241 may pass through the notches on the surfaces of the plurality orthodontic correction units 31, so as to enable the teeth of the patient to have a corrective force. In accordance with the fifth preferred exemplary embodiment of the present invention, the elastic member 24 may be configured as a orthodontic wire body 241. The dental surgeon may enable one end of the orthodontic wire body 241 to be fixed on the fixing member 21 of the bone screw plate 20 in accordance with the status of each of the teeth. Another end of the orthodontic wire body 241 may be in mutual connection with the correction portion 231 on one of the orthodontic correction units 31 of the orthodontic appliance 3. The orthodontic wire body 241 may include a bending portion 241a that has a bending angle, so as to enable the orthodontic wire body 241 to form a tension between the fixing member 21 and the connecting portion 231. As such, the tension may enable the teeth of the patient to receive an inward pulling force.

Figure 13:
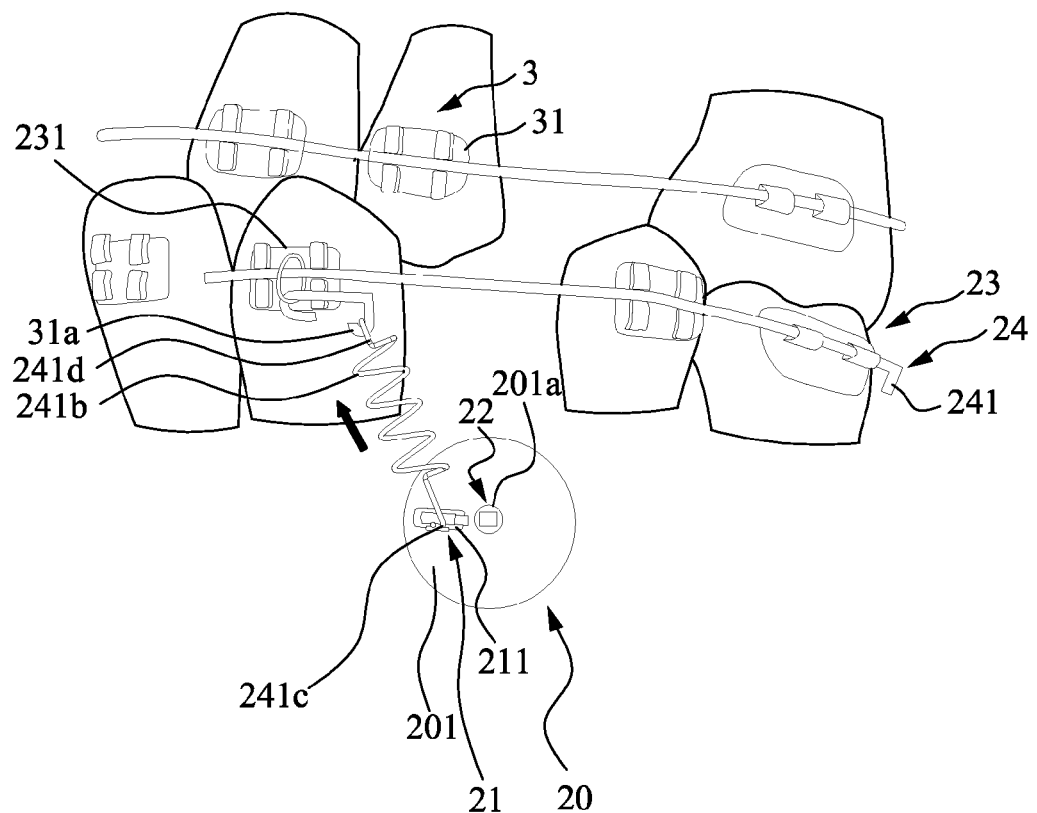
FIG. 13 is a schematic diagram showing the orthodontic correction device that is in use in accordance with the sixth preferred exemplary embodiment of the present invention.

In accordance with the sixth preferred exemplary embodiment of the present invention, and as shown in FIG. 13, the elastic member 24 may still be the orthodontic wire body 241. The wire segment region between the fixing end 241c and the functioning end 241d of the orthodontic wire body 241 may be bent so as to form an elastic portion 241b that is in an elastic form. Also, the functioning end 241d of the orthodontic wire body 241 may be hooked on to the hook portion 31a on one of the plurality of orthodontic correction units 31 of the orthodontic appliance 3. In other words, the length of the wire segment of the elastic portion 241b may be limited and may be compressed by the fixing member 21 and the connecting portion 231, such that a restoring force may be generated on the teeth of the patient. As such, the restoring force may enable the teeth of the patient to receive an outward pushing force.

Figure 14:
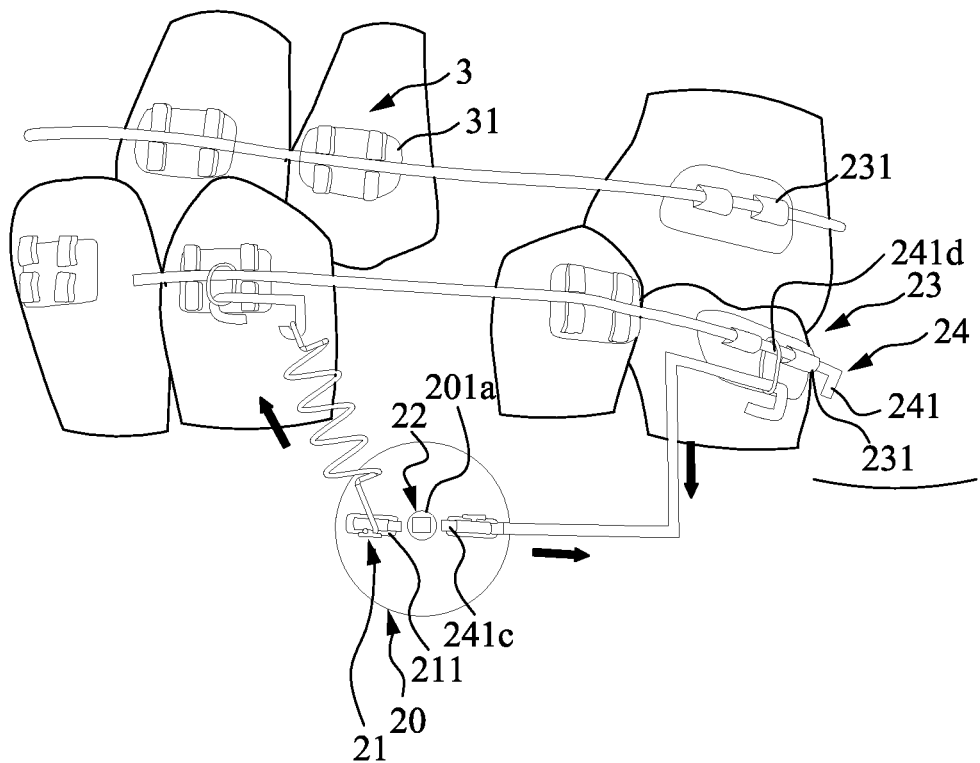
FIG. 14 is a schematic diagram showing the orthodontic correction device that is in use and that carries out a pulling force or a pushing force at the same time, in accordance with the present invention.

The fifth preferred exemplary embodiment and the sixth preferred exemplary embodiment of the present invention may use the same bone screw plate 20 at the same time, as shown in FIG. 14. As such, the same bone screw plate 20 may be enabled to perform the action of the outward pushing force and the action of an inward pulling force for a single tooth or a number of teeth at the same time.

Figure 15:
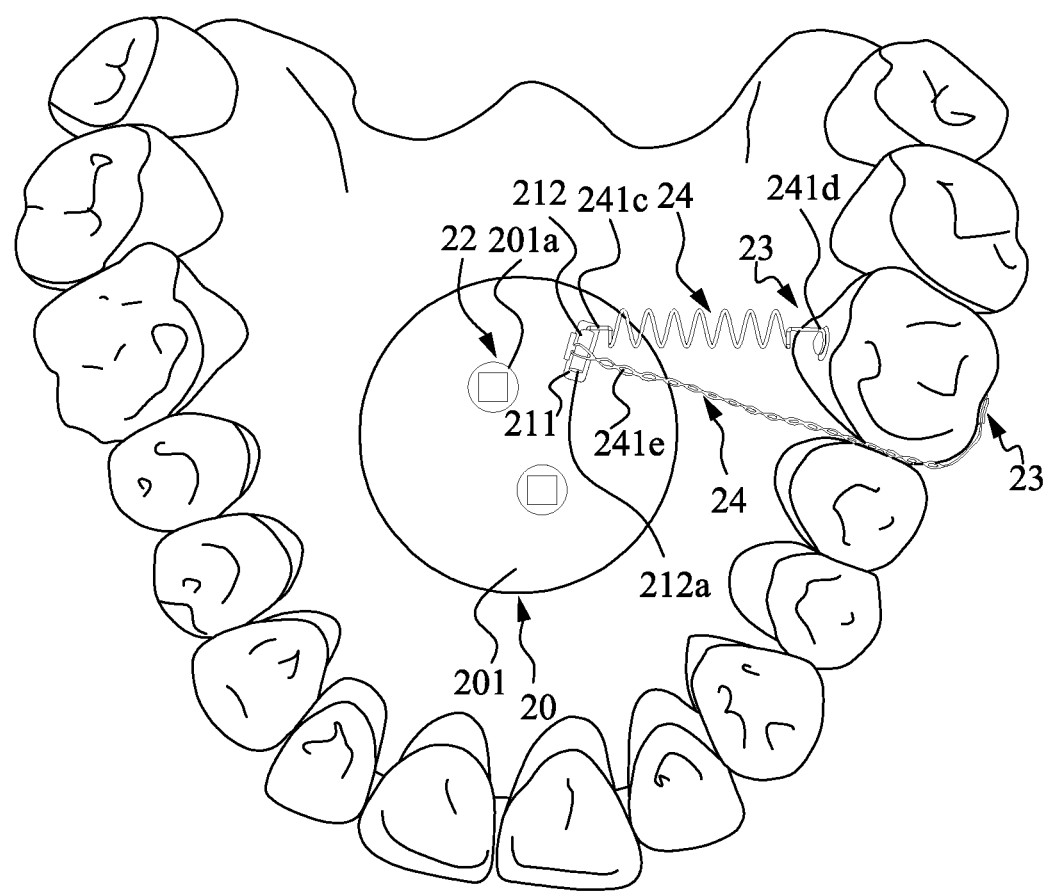
FIG. 15 is a schematic diagram showing the orthodontic correction device that is in use and is used for rotating a single tooth in accordance with the seventh preferred exemplary embodiment of the present invention.

The seventh exemplary embodiment shows that the orthodontic correction device 2 of the present invention is being used for the orthodontic correction of a single tooth of the patient. As shown in FIG. 15, a plurality of seat bodies 23 are set up on the teeth, and in addition, an elastic member 24 that may exert a pushing force and another elastic member 24 that may exert a pulling force are used on a single tooth of the patient; that is, this method may enable the single tooth to have a rotational torque, and enabling the teeth that are misaligned to be corrected in the expected manner. The orthodontic correction device 2 of the seventh preferred exemplary embodiment of the present invention may also be used in conjunction with the orthodontic correction device 2 that is within the first to the sixth exemplary embodiment of the present invention. This may enable the dental surgeon to carry out orthodontic correction of a single tooth or a number of teeth of the patient at the same time by means of the bone screw plate 20, and this in turn enables a number of teeth of the patient to be pulled closer synchronously, such that the distance of the multiple teeth of the patient is much closer. This has the effect of pushing the distance of the teeth and/or enabling a single tooth of the patient to have a torque force that rotates at an angle.

Figure 16:
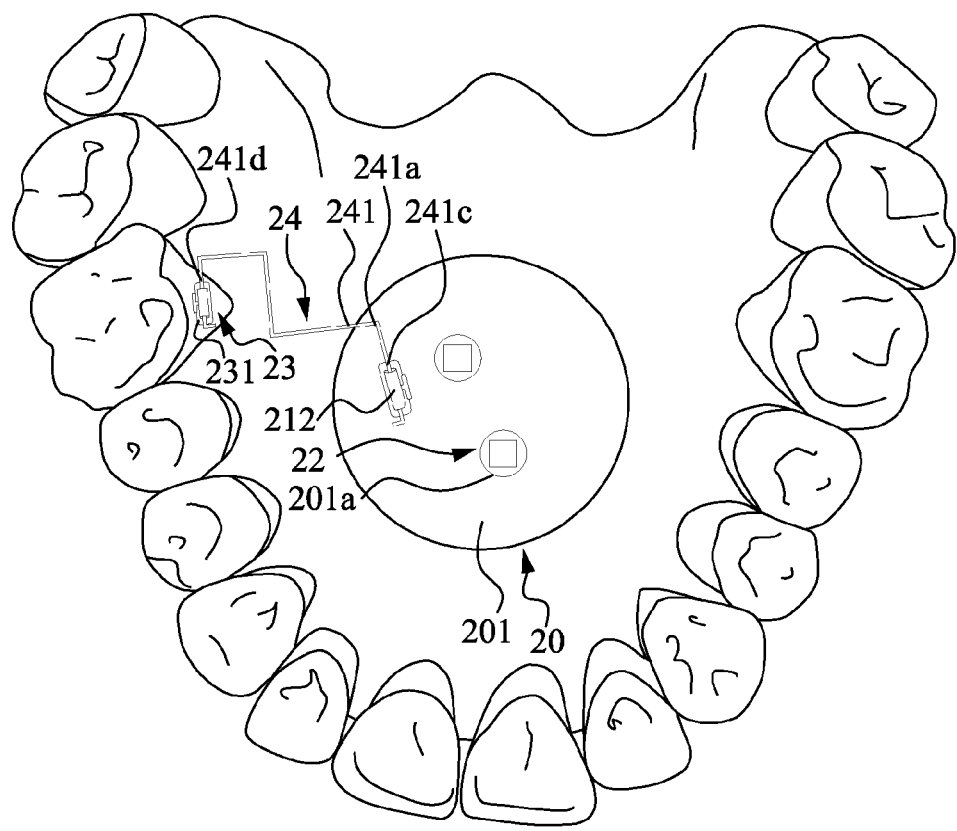
FIG. 16 is another schematic diagram showing the orthodontic correction device that is in use and is used for rotating a single tooth in accordance with the seventh preferred exemplary embodiment of the present invention.

In accordance with another example of the seventh preferred exemplary embodiment of the present invention, and as shown in FIG. 16, the orthodontic wire body 241 may include at least a bending portion 241a that has a bending angle. In addition, the orthodontic wire body 241 may be in mutual connection with the connecting portion 231. In accordance with the seventh preferred exemplary embodiment of the present invention, the connecting portion 231 and the fixing member 21 may configured to be the same, so as to enable the orthodontic wire body 241 to pass through and to be fixed at the connecting portion 231. Moreover, each of the teeth of the patient may be rotated in accordance with the offset status of the teeth, by means of the bending angle of the bending portion 241a.

In view of all of the above, the advantage of the present invention is that the orthodontic correction device 2 of the present invention can enable the orthodontic correction of a number of teeth in different locations and teeth that have different statuses in the oral cavity of the patient, and this can be achieved by the use of the fixing member 21 which is on the bone screw plate 20, and the fixing member 21 on the bone screw plate 20 is used in conjunction with at least an elastic member 24 that has a pulling force, or at least an elastic member 24 that has a pushing force. Also, the orthodontic correction device 2 of the present invention can carry out orthodontic correction of single tooth of the patient by exerting a multidirectional corrective force; and furthermore, as to the orthodontic correction of a number of teeth of the patient, the orthodontic correction can be achieved by the corrective force being exerted together at the same time on the number of teeth of the patient. As such, the orthodontic correction device 2 of the present invention can also enable the quantity of the bone screw to be inserted into the oral cavity of the patient to be reduced. Moreover, another advantage of the orthodontic correction device 2 of the present invention is that the point of exertion of the correct force as well as the direction of the torque force on the bone screw plate 20 and on the teeth of the patient can be accurately adjusted, by means of changing the direction and location of the fixing member 21 of the orthodontic correction device 2. In other words, the multifunctional orthodontic bone screw plate 20 of the present invention is not only able to significantly increase the efficiency of the orthodontic treatment offered by the dental surgeon, and the pain and fear experienced by the orthodontic patients during the orthodontic treatment process can also be reduced. Furthermore, the safety of the implantation surgery for orthodontic correction of the patients can also be further increased.

Although the preferred exemplary embodiments of the present invention have been described with reference to the preferred exemplary embodiments thereof, it may be apparent to those ordinarily skilled in the art that a variety of modifications and changes may be made without departing from the scope of the present invention which is intended to be defined by the appended claims.

What is claimed is:

1. An orthodontic correction device configured for insertion within a patient's oral cavity for correcting an arrangement of teeth, the orthodontic correction device comprising:
    a bone screw member having a plate comprised of at least one positioning portion that defines a fixing area surrounding a periphery of the plate and having a surface that includes a fixing member;
    multiple fixing members disposed on the fixing area and comprising:
        an engagement portion;
        a base portion having at least two sides and an edge, one side of the base portion being provided adjacent to the surface of the plate, another side of the base portion being connected to the engagement portion, provided that the edge of the base portion of the multiple fixing members does not extend beyond the fixing area; and
        at least a fixing member selectivity connected at an arbitrary position of the fixing area;
    at least one bone screw connected to the at least one positioning portion of the bone screw member, and fixed by implantation into the patient's oral cavity;
    at least one base body assembled on a surface of the teeth, and comprising a connecting portion;
    multiple elastic members each having a fixing end and a functioning end, the fixing end being assembled on the engagement portion, the functioning end being connected to the connecting portion of the base body mutually, and an orthodontic correction force being formed between the fixing end and the functioning end,
    wherein multiple orthodontic correction forces acting in different directions are formed by the multiple fixing members and the base body, and
    wherein the engagement portion comprises at least a through hole, and the elastic member is configured as an orthodontic wire body that is bent and fixed at the through hole.

2. The orthodontic correction device in accordance with claim 1, wherein the engagement portion further comprises an opening that is in connection with the through hole.

3. The orthodontic correction device in accordance with claim 1, wherein the orthodontic wire body comprises a bending portion that has a bending angle.

4. The orthodontic correction device in accordance to claim 1, wherein the orthodontic wire body forms an elastic portion by bending in between the fixing end and the functioning end.

5. The orthodontic correction device in accordance with claim 1, wherein the engagement portion comprises at least a hook, and the elastic member comprises at least a housing aperture that is fixed on the hook.

6. The orthodontic correction device in accordance with claim 1, wherein the connecting portion is configured as an orthodontic monomer that is in connection with the teeth.

* * * * *